US007767640B2

(12) United States Patent
Finke et al.

(10) Patent No.: US 7,767,640 B2
(45) Date of Patent: Aug. 3, 2010

(54) MIXTURES FOR USE AS MUSK FRAGRANCE

(75) Inventors: Anja Finke, Holzminden (DE); Steffen Sonnenberg, Holzminden (DE)

(73) Assignee: Symrise GmbH & Co. KG, Holzminden (DE)

( * ) Notice: Subject to any disclaimer, the term of this patent is extended or adjusted under 35 U.S.C. 154(b) by 546 days.

(21) Appl. No.: 10/493,531

(22) PCT Filed: Oct. 14, 2002

(86) PCT No.: PCT/EP02/11472

§ 371 (c)(1),
(2), (4) Date: Apr. 22, 2004

(87) PCT Pub. No.: WO03/038019

PCT Pub. Date: May 8, 2003

(65) Prior Publication Data

US 2005/0037037 A1 Feb. 17, 2005

(30) Foreign Application Priority Data

Oct. 26, 2001 (DE) ................................ 101 52 992

(51) Int. Cl.
*A61K 8/00* (2006.01)
*A61K 8/18* (2006.01)

(52) U.S. Cl. ............................ 512/27; 512/1; 514/675; 424/400

(58) Field of Classification Search ....................... None
See application file for complete search history.

(56) References Cited

U.S. PATENT DOCUMENTS

| | | | | |
|---|---|---|---|---|
| 3,681,396 | A * | 8/1972 | Mookherjee et al. | 549/272 |
| 3,890,353 | A * | 6/1975 | Becker | 549/266 |
| 3,935,270 | A * | 1/1976 | Calderon | 568/365 |
| 5,266,559 | A * | 11/1993 | Fankhauser et al. | 512/11 |
| 6,057,372 | A * | 5/2000 | Nobuhiro et al. | 514/675 |
| 6,815,413 | B2 * | 11/2004 | Eh et al. | 512/27 |
| 7,208,463 | B2 * | 4/2007 | Heltovics et al. | 512/1 |

FOREIGN PATENT DOCUMENTS

| | | | |
|---|---|---|---|
| EP | 0 424 787 | A | 5/1991 |
| EP | 1 201 738 | A | 5/2002 |
| GB | 922 409 | A | 4/1963 |
| GB | 1 266 091 | A | 3/1972 |
| JP | 2001-152177 | A | 6/2001 |
| JP | 2001-163744 | A | 6/2001 |
| WO | WO 98 32820 | A | 7/1998 |

OTHER PUBLICATIONS

Korber et al., Influence of Molecular Structure upon the Musk Odor Characteristics of Macrocyclic Ketones, 1980, Fragrance Flavour Substances, 46FHA6, p. 155-166.*

(Continued)

*Primary Examiner*—Robert A Wax
*Assistant Examiner*—Melissa S Mercier
(74) *Attorney, Agent, or Firm*—Novak Druce + Quigg; Gregory A. Nelson; Gregory M. Lefkowitz

(57) ABSTRACT

The present invention relates to novel mixtures of macrocyclic musk fragrances, the use of these mixtures in fragrance compositions and perfumed products containing these mixtures.

15 Claims, 4 Drawing Sheets

OTHER PUBLICATIONS

Arctander S.:"Perfume and Flavor Chemicals (Aroma Chemicals)" 1969, Perfume and Flavor Chemicals (Aroma Chimicals). A-J, Monclair, S. Arctander, US vol. 1, p. 771 XP002164610.

H.H.Mathur and S.C.Bhattacharyya: "Macrocyclic Musk Compounds-IX" Tetrahedron, Bd. 21, 1965, Sides 1537-1540, XP002230767, Pergamon Press Ltd, Northern Ireland.

* cited by examiner

MIXTURES FOR USE AS MUSK FRAGRANCE

CROSS REFERENCE TO RELATED APPLICATION

This application is a national stage of PCT/EP02/11472 filed Oct. 14, 2002 and based upon DE 101 52 992.9 filed Oct. 26, 2001, under the International Convention.

FIELD OF THE INVENTION

The present invention relates to novel mixtures of macrocyclic musk fragrances, the use of these mixtures in fragrance compositions and perfumed products containing these mixtures.

BACKGROUND OF THE INVENTION

Fragrances are used in numerous products to improve the odor. The impression of freshness and cleanliness in the case of, for example, air fresheners and also detergents and cleaning agents can be distinctly intensified by perfuming. The use of fragrances therefore constitutes a product improvement.

Compounds with a musk odor play an exceptional role in the perfume industry. Because of their unique property of harmonizing fragrance compositions, imparting personality to them and at the same time increasing their bonding, musk fragrances are nowadays found in considerable amounts in virtually every perfume oil. Accordingly, the annual world demand for musk fragrances is several thousand tonnes. The major proportion is made up of the so called “polycyclic aromatic” musk bodies. Typical representatives of this class of compounds are, for example, 1,3,4,6,7,8,8-hexahydro-4,6,6,8-hexamethylcyclopenta-(g)-2-benzopyrane (1) and 6-acetyl-1,1,2,4,4,7-hexamethyltetralin (2).

It is known that polycyclic aromatic musk fragrances are poorly biodegradable and, as extremely lipophilic compounds, display bioaccumulative behaviour, i.e. are able to accumulate in the fatty tissue of living organisms.

Macrocyclic musk fragrances, on the other hand, are accepted as biodegradable (R. Fenn, 1999, Perfumer & Flavorist, pp. 17-27; H. Gebauer, T. Bouter, 1997, Euro Cosmetics, pp.

In general, however, because of the generally increasing sensitization, it is of interest to keep the amounts of fragrances that pass into the environment as low as possible.

Mixtures of cylcopentadecanone (3), hexadecanolide (4) and pentadecanolide (oxacyclohexadecan-2-one) (5) are described in WO 98/32820 as particularly substantive on skin, hair and textile fibres.

Further mixtures are described as the direct product from the synthesis, such as in the case of cyclic ethylene glycol dodecanedioate (6) and ethylene glycol undecanedioate (7) (EP-A 905 222) or cyclotridecanolide (8), cyclotetradecanolide (9) and cyclopentadecanolide (5) (JP 2001/152177).

There is an urgent need for musk fragrances which have an odor that is stronger than that of the known macrocyclic musk fragrances.

SUMMARY OF THE INVENTION

The mixtures according to the invention surprisingly have a stronger odor than the individual substances in the same amount.

The invention therefore relates to mixtures containing

I) cis/trans-8-cyclohexadecen-1-one (10 and

II) cis/trans-12/13-oxacyclohexadecen-2-one (11) or oxacyclohexadecan-2-one (5) or I) cyclohexadecanone (12) and II) cis/trans-12/13-oxacyclohexadecen-2-one (11) or oxacyclohexadecan-2-one (5) or I) cis/trans-8-cyclohexadecen-1-one (10) and II) cyclohexadecanone (12)

The individual musk fragrances have the following structures:

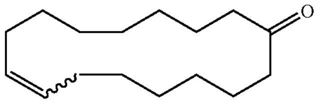

10

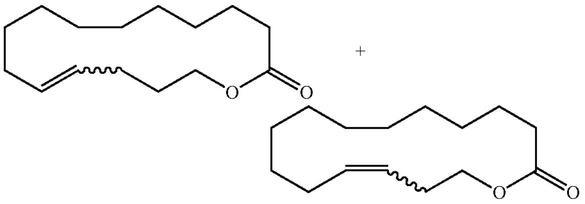

11

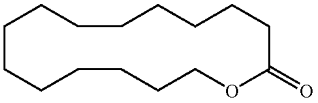

5

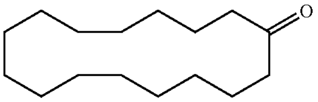

12

DETAILED DESCRIPTION

Figure 1:
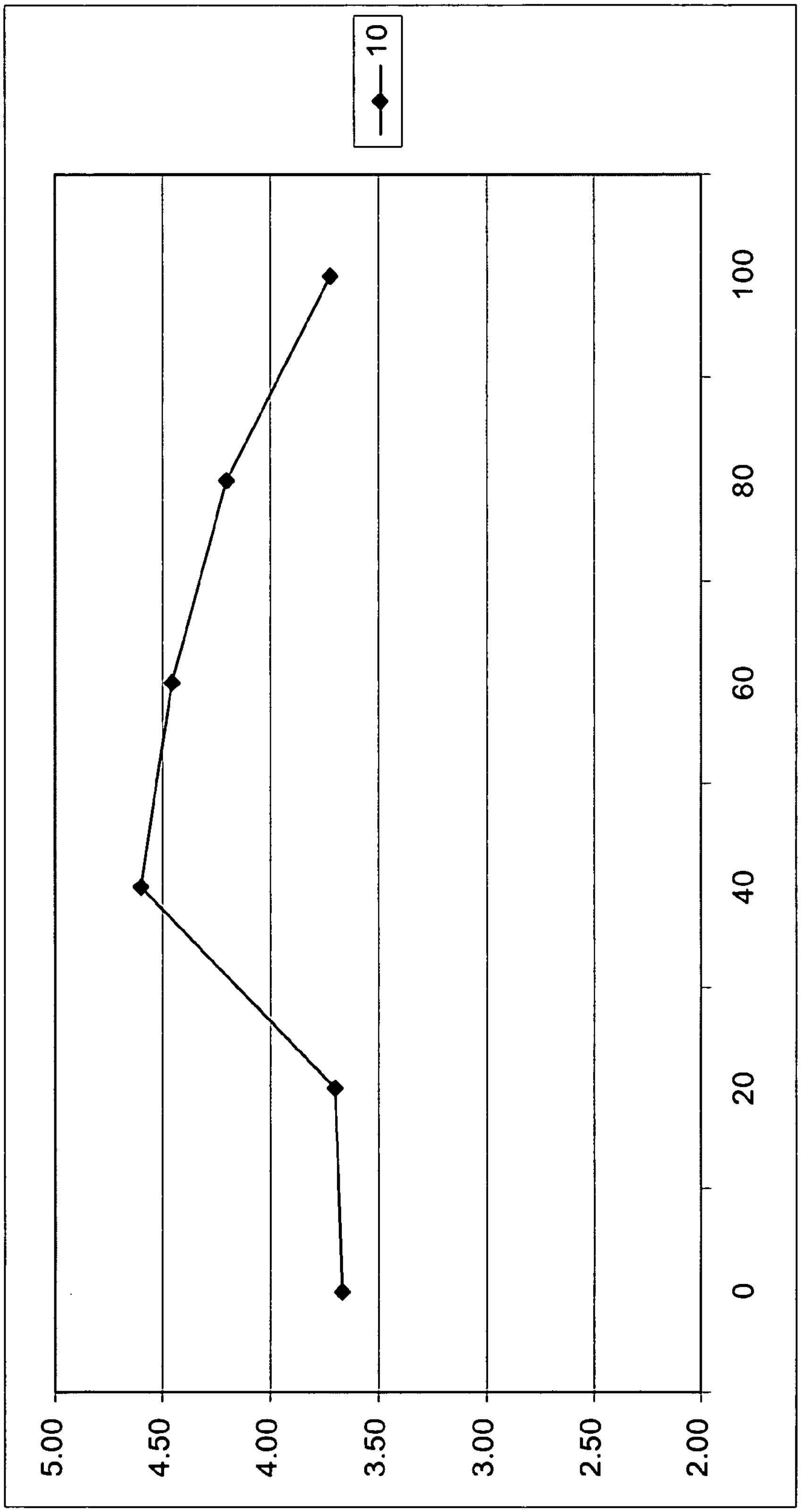
FIG. 1 shows the intensities of mixtures of 10 with 11 on perfume strips.

For the same amount used, these mixtures of various musk fragrances display a higher intensity than the relevant individual fragrances. As a result of this synergistic effect, the mixtures on their own and products perfumed therewith are perceived more strongly. A considerable advantage in use is achieved.

The intensity of a substance or substance mixture describes the strength of the odor impression. The stronger the odor of a substance or substance mixture, the higher is the value for the intensity.

The fragrances were dipped on their own and as mixtures in various compositions on perfume strips and assessed by a trained group of experts with at least 12 participants (tester group). The testers assessed the intensity. Different ratios of fragrances with respect to one another showed different results. It was found that certain ratios of fragrances were surprisingly particularly intense.

Furthermore, fragrances were incorporated, on their own and as mixtures in various compositions, into various products. The intensity in different application stages of the products concerned was assessed by a tester group. It was found that certain ratios of fragrances were surprisingly particularly intensive in use.

Mixtures characterized in that the ratio of 10 to 5 or 11 is between 4:1 and 1:4 are preferred; particularly preferentially the ratio of 10 to 5 or 11 is between 2:1 and 1:2 and especially preferentially between 3.2 and 2.3.

Mixtures characterized in that the ratio of 12 to 5 or 11 is between 9:1 and 2:3, particularly preferentially between 6:1 and 1:1 and especially preferentially between 4.1 and 3.2 are preferred.

Mixtures characterized in that the ratio of 10 to 12 is between 9:1 and 2:3, particularly preferentially between 6:1 and 1:1 and especially preferentially between 4:1 and 3:2 are particularly suitable.

A further part of the invention relates to fragrance compositions that contain the mixtures according to the invention.

Fragrance compositions containing 0.01-60% (m/m), preferably 0.1-40% (m/m) and particularly preferentially 1.5-25% (m/m) of the mixtures according to the invention are particularly suitable.

As a result of the higher intensity of the substance mixtures found, it is possible to use a smaller amount of the mixture in perfumed products, compared with the individual substances. This is advantageous with a view to the environment. Furthermore, a perfumer retains a greater freedom in creation, since the latter as a rule has a price limit for the costs of a perfume oil.

It has been found that, when the mixtures according to the invention are used, a different concentration ratio can arise in the gas space above the product, depending on the rate of evaporation and on the formulation-dependent release from perfumed products. Similarly, the concentrations in the gas space above perfumed products used, for example aqueous solutions thereof or substrates perfumed by these products, such as, for example, skin, hair, wool, cotton and synthetic materials, can deviate from the ratios in the perfume mixture.

Moreover, it has been found that the mixtures have a particularly good affinity for wool, cotton, skin, hair, synthetic materials and smooth and structured surfaces.

Furthermore, a fixing action on other constituents of a perfuming and an effect of intensifying other fragrances in perfumed products ("booster" effect) were found.

The fragrances present in the mixtures according to the invention can be prepared in accordance with syntheses described in the literature, for example the syntheses of 10 and 12 according to Mookherje, Trenkle and Patel (Journal of Organic Chemistry, 1971, pp. 3266-3270), of 11 according to Ogibin, Terent'ev und Nikishin (Russian Chemical Bulletin, 1998, pp. 1166-1169) and of 5 according to Ohloff (Riechstoffe and Geruchssinn. Die molekulare Welt der Düifte, Springer Verlag, Berlin, 1990, pp. 200 et seq.), or are available commercially.

The mixtures according to the invention are particularly suitable for combination with further musk fragrances such as, for example, 1,4-dioxacycloheptadecan-5,17-dione, cis-4-cyclopentadecenone, 3-methylcyclopentadecanone, 1,7-dioxacycloheptadecan-8-one, oxacycloheptadec-8-en-2-one, 5-cyclohexadecen-1-one, cyclopentadecanone, 3-methylcyclopentadec-4-enone/3-methylcyclopentadec-5-enone, 1,3,4,6,7,8,8-hexahydro-4,6,6,8-hexamethylcyclopenta-(g)-2-benzopyrane (1) and 6-acetyl-1,1,2,4,4,7-hexamethyltetralin (2).

Examples of fragrances with which the mixtures according to the invention can be combined are given, for example, in K. Bauer, D. Garbe and H. Surburg, Common Fragrance and Flavor Materials, 3$^{rd}$. Ed., Wiley-VCH, Weinheim 1997.

The following particularly suitable fragrances may be mentioned individually:

extracts from natural raw materials such as essential oils, concretes, absolutes, resins, resinoids, balsams, tinctures, such as, for example, ambergris tincture; amyris oil; angelica seed oil; angelica root oil; aniseed oil; valerian oil; basil oil; wood moss absolute; bay oil; mugwort oil; benzoin resin; bergamot oil; beeswax absolute; birch tar oil; bitter almond oil; savory oil; bucho leaf oil; cabreuva oil; cade oil; calamus oil; camphor oil; cananga oil; cardamom oil; cascarilla oil; cassia oil; cassia absolute; castoreum absolute; cedar leaf oil; cedarwood oil; cistus oil; citronella oil; lemon oil; copaiva balsam; copaiva balsam oil; coriander oil; costus root oil; cumin oil; cypress oil; davana oil; dill herb oil; dill seed oil; eau de brouts absolute; oakmoss absolute; elemi oil; tarragon oil; eucalyptus citriodora oil; eucalyptus oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; camomile oil blue; Roman camomile oil; carrot seed oil; cascarilla oil; pine needle oil; spearmint oil; caraway oil; labdanum oil; labdanum absolute; ladanum resin; lavandin absolute; lavandin oil; lavender absolute; lavender oil; lemongrass oil; lovage oil; distilled lime oil; pressed lime oil; linaloe oil; litsea cubeba oil; bayleaf oil; mace oil; marjoram oil; mandarin oil; massoi bark oil; mimosa absolute; musk seed oil; musk tincture; clary oil; nutmeg oil; myrrh absolute; myrrh oil; myrtle oil; clove leaf oil; clove blossom oil; neroli oil; olibanum absolute; olibanum oil; opopanax oil; orange blossom absolute; orange oil; origanum oil; palmarosa oil; patchouli oil; perilla oil; Peruvian balsam oil; parsley leaf oil; parsley seed oil; petitgrain oil; peppermint oil; pepper oil; pimenta oil; pine oil; pennyroyal oil; rose absolute; rosewood oil; rose oil; rosemary oil; Dalmation sage oil; Spanish sage oil; sandalwood oil; celery seed oil; spike lavender oil; Japanese anise oil; styrax oil; tagetes oil; fir needle oil; tea tree oil; turpentine oil; thyme oil; Tolu balsam; tonka absolute; tuberose absolute; vanilla extract; violet leaf absolute; verbena oil; vetiver oil; juniper oil; wine lees oil; absinthe oil; wintergreen oil; ylang oil; hyssop oil; civet absolute; cinnamon leaf oil; cinnamon bark oil; and fractions thereof or constituents isolated therefrom;

individual fragrances from the group comprising the hydrocarbons, such as, for example, 3-carene; α-pinene; β-pinene; α-terpinene; γ-terpinene; p-cymene; bisabolene; camphene; caryophyllene; cedrene; famesene; limonene; longifolene; myrcene; ocimene; valencene; (E,Z)-1,3,5-undecatriene;

the aliphatic alcohols, such as, for example, hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; the aliphatic aldehydes and the 1,4-dioxacycloalken-2-ones thereof, such as, for example, hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyloxyacetaldehyde;

the aliphatic ketones and oximes thereof, such as, for example, 2-heptanone; 2-octanone; 3-octanone; 2-nonanone; 5-methyl-3-heptanone; 5-methyl-3-heptanone oxime; 2,4,4,7-tetramethyl-6-octen-3-one; the aliphatic sulphur-containing compounds, such as, for example, 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol; the aliphatic nitriles, such as, for example, 2-nonenoic acid nitrile; 2-tridecenoic acid nitrile; 2,12-tridecenoic acid nitrile; 3,7-dimethyl-2,6-octadienoic acid nitrile; 3,7-dimethyl-6-octenoic acid nitrile;

the aliphatic carboxylic acids and esters thereof, such as, for example, (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate, isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynoate; methyl 2-nonynoate; allyl 2-isoamyloxyacetate; methyl 3,7-dimethyl-2,6-octadienoate;

the acyclic terpene alcohols, such as, for example, citronellol; geraniol; nerol; linalool; lavandulol; nerolidol; famesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates and 3-methyl-2-butenoates thereof;

the acyclic terpene aldehydes and ketones, such as, for example, geranial; Neral; cirtonellal; 7-hydroxy-3,7-dimethyloctanal; 7-methoxy-3,7-dimethyl-octanal; 2,6,10-trimethyl-9-undecenal; geranylacetone; and the dimethyl and diethyl acetals of geranial, Neral and 7-hydroxy-3,7-dimethyloctanal;

the cyclic terpene alcohols, such as, for example, menthol; isopulegol; alpha-terpineol; terpineol-4; menthan-8-ol; menthan-1-ol; menthan-7-ol; borneol; isobomeol; linalool oxide; nopol; cedrol; ambrinol; vetiverol; guaiol; and formates, acetates, propionates, isobutyrates, butyrates, isovalerates, pentanoates, hexanoates, crotonates, tiglinates and 3-methyl-2-butenoates thereof; the cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal and acetylated cedarwood oil (methyl cedryl ketone);

the cyclic alcohols, such as, for example, 4-tert-butylcyclohexanol; 3,3,5-trimethylcyclohexanol; 3-isocamphylcyclohexanol; 2,6,9-trimethyl-Z2, Z5, E9-cyclododecatrien-1-ol and 2-isobutyl-4-methyltetrahydro-2H-pyran-4-ol;

the cycloaliphatic alcohols, such as, for example, alpha-3,3-trimethyl-cyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol and 1-(2,2,6-trimethylcyclo-hexyl)hexan-3-ol;

the cyclic and cycloaliphatic ethers, such as, for example, cineole; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide and 2-(2,4-dimethyl-3-cyclohexen-1-yl)-5-methyl-5-(1-methylpropyl)-1,3-dioxane;

the cyclic ketones, such as, for example, 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 6,7-dihydro-1,1,2,3,3-pentamethyl-4(5H)-indanone; 5-cyclohexadecen-1-one; 8-cyclohexadecen-1-one; cyclopentadecanone;

the cycloaliphatic aldehydes, such as, for example, 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde and 4-(4-methyl-3-penten-1-yl)-3-cyclohexenecarbaldehyde;

the cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone and tert-butyl 2,4-dimethyl-3-cyclohexen-1-yl ketone;

the esters of cyclic alcohols such as, for example, 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate and 4,7-methanooctahydro-5 or 6-indenyl acetate;

the esters of cycloaliphatic carboxylic acids, such as, for example, allyl 3-cyclohexylpropionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate and ethyl 2-methyl-1,3-dioxolane-2-acetate;

the aromatic hydrocarbons, such as, for example, styrene and diphenylmethane;

the araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methyl-phenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol and 1-(4-isopropylphenyl)ethanol;

the esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; the araliphatic ethers, such as, for example, 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropic aldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

the aromatic and araliphatic aldehydes, such as, for example, benzaldehyde; phenylacetaldehyde; 3-phenylpropanal; hydratropic aldehyde; 4-methylbenzaldehyde; 4-methylphenylacetaldehyde; 3-(4-ethylphenyl)-2,2-dimethylpropanal; 2-methyl-3-(4-isopropyl-phenyl)propanal; 2-methyl-3-(4-tert-butylphenyl)propanal; 3-(4-tert-butyl-phenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxy-benzaldehyde; 4-hydroxy-3-ethoxybenzaldehyde; 3,4-methylenedioxybenzaldehyde; 3,4-dimethoxybenzaldehyde; 2-methyl-3-(4-methoxy-phenyl)propanal and 2-methyl-3-(4-methylenedioxyphenyl)propanal;

the aromatic and araliphatic ketones, such as, for example, acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone and 5',6',7',8'-tetrahydro-3',5',5',6',8',8'-hexamethyl-2-acetonaphthone;

the aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate and ethyl 3-methyl-3-phenylglycidate;

the nitrogen-containing aromatic compounds, such as, for example, 2,4,6-trinitro-1,3-dimethyl-5-tert-butylbenzene; 3,5-dinitro-2,6-dimethyl-4-tert-butylacetophenone; cinnamonitrile; 5-phenyl-3-methyl-2-pentenoic acid nitrile; 5-phenyl-3-methylpentanoic acid nitrile; methyl anthranilate; methyl N-methylanthranilate; Schiffs bases of methyl anthranilate with 7-hydroxy-3,7-dimethyloctanal; 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; indole; scatole; 2-methoxy-3-isopropylpyrazine and 2-isobutyl-3-methoxypyrazine;

the phenols, phenyl ethers and phenyl esters, such as, for example, estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol and p-cresyl phenylacetate;

the heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one and 2-ethyl-3-hydroxy-4H-pyran-4-one;

the lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin and octahydrocoumarin.

The mixtures can be combined very well with other fragrances in various, different mixing ratios to give novel fragrance compositions, for example perfume oils.

These fragrance compositions can be used in so-called perfumed products, such as, for example, household products, bodycare and perfumery products.

Particularly preferred perfumed products, are, for example, alcoholic fine perfumes, washing powders, soft rinses, soft rinse cloths, surface cleaners, toilet cleaners, rinses, all-purpose cleaners, disinfectants, polishes, glass cleaners, washing-up liquids, air fresheners, shampoos, conditioners, hair colourants, deodorants, antiperspirants, solid and liquid soaps, body lotions, skin creams and waxes.

EXAMPLES

The mixtures of the individual fragrances are prepared in the ratios 100:0, 80:20, 60:40, 40:60, 20:80 and 0:100%.

An independent trained group of experts made up of at least 12 persons (tester group) assesses the intensities of the individual samples and the detection limit thereof.

In all examples the samples were coded with combinations of letters and numerals for the assessment. This coding is redone for each test. The samples are provided for smelling in different sequences.

The ratio of cis to trans in the 8-cyclohexadecen-1-one (10) used here was 3:7.

Example 1

Intensity of Perfume Strips

Perfume strips are dipped into the various mixtures and covered with plastic sleeves. All mixtures are prepared as a 50% (m/m) solution in isopropyl myristate. The testers smell and assess the strips. The samples are assessed on a scale of 1=odorless to 6=very strong odor.

Figure 2:
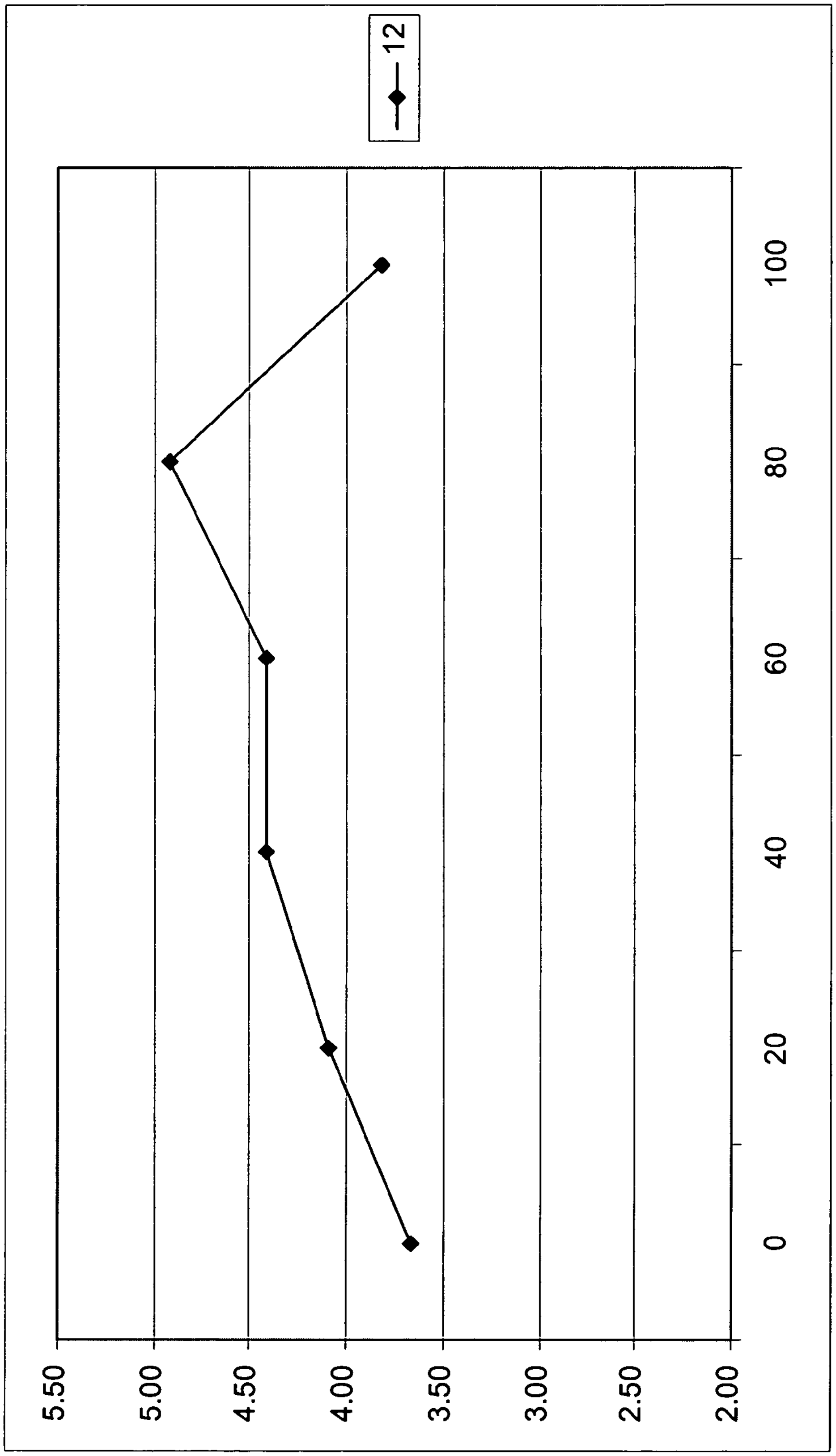
FIG. 2 shows the intensities of mixtures of 12 with 11 on perfume strips.
Figure 3:
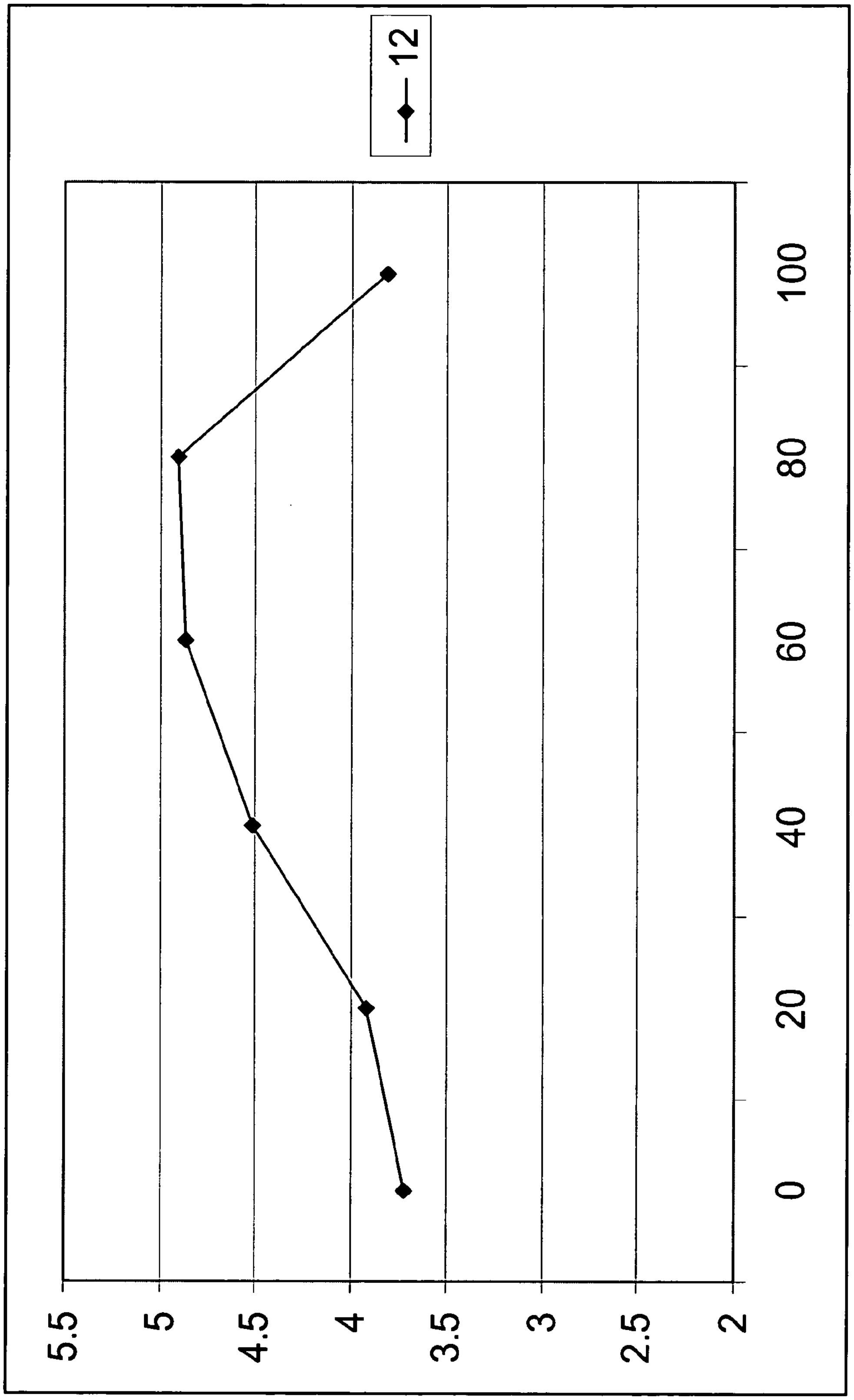
FIG. 3 shows the intensities of mixtures of 10 with 12 on perfume strips.

An average is formed from the values obtained and plotted in a graph (FIGS. 1-3). In each case the proportions of the indicated components in the mixture in percent are plotted on the x-axis and the intensities on the scale of 1-6 on the y-axis. FIG. 1 shows the intensities of mixtures of 10 with 11 on the perfume strips. FIG. 2 shows the intensities of mixtures of 12 with 11 on the perfume strips. FIG. 3 shows the intensities of mixtures of 10 with 12 on the perfume strips.

The synergy effects are clearly discernible in the diagrams. Virtually all mixtures have a higher intensity than the individual fragrances (0 and 100%, respectively). Certain ratios in each case have a particularly high intensity.

Application Examples

Example 2

Musk Mixtures in Shampoo

An example formulation for a perfumed shampoo is as follows:

TABLE 1

1. Shampoo, clear

| Constituents | INCI name | % (m/m) |
|---|---|---|
| Plantacare PS 10 (1) | Sodium Laureth Sulfate (and) Lauryl Glycoside | 20.000 |
| Demineralised water | Water (Aqua) | 5.450 |
| Sodium chloride | Sodium Chloride | .400 |
| Phenonip (2) | Phenoxyethanol (and) Methyl paraben (and) Ethylparaben (and) Propylparaben (and) Butylparaben | 0.500 |
| Citric acid 10.0% solution | Citric Acid | .650 |
| Perfume oil (3) | Fragrance | .000 |

Suppliers:

Cognis Deutschland GmbH, D-40191 Dusseldorf, Germany

Nipa Laboratories Ltd., CF382SN South Wales, UK

Haarmann & Reimer GmbH, D-37603 Holzminden, Germany

The following fragrances and musk mixtures are tested: 5, 11, 12, 10, 2:1 of 10:5, 2:1 of 12:11, 1:1 of 10:11, 3:2 of 12:5 and 4:1 of 12:10. All fragrances and mixtures are used as a 50% (m/m) solution in isopropyl myristate as perfume oil.

The various musk mixtures are incorporated in the indicated amount in the shampoo composition for perfuming.

All use steps of a shampoo are assessed in the sensory evaluation. For this purpose 10 g aliquots of the shampoos are filled into screw-cap tubes. 20 g of 20% (m/m) aqueous solution is also prepared from each of the shampoos. In each case two hair strands that have previously been washed until neutral are washed for 2 minutes in 100 ml of a 20% (m/m) solution and then rinsed for 20 s under hand-hot, running water. The hair strands are combed and in each case one is wrapped wet in aluminum foil and the other is hung up to dry.

At least 12 trained testers assess the intensities of the coded samples in varying sequence. The dry hair is assessed first, then the wet hair, the solutions and finally the pure shampoos.

The samples are ranked on a scale of 1=odorless to 6=very strong odor.

Figure 4:
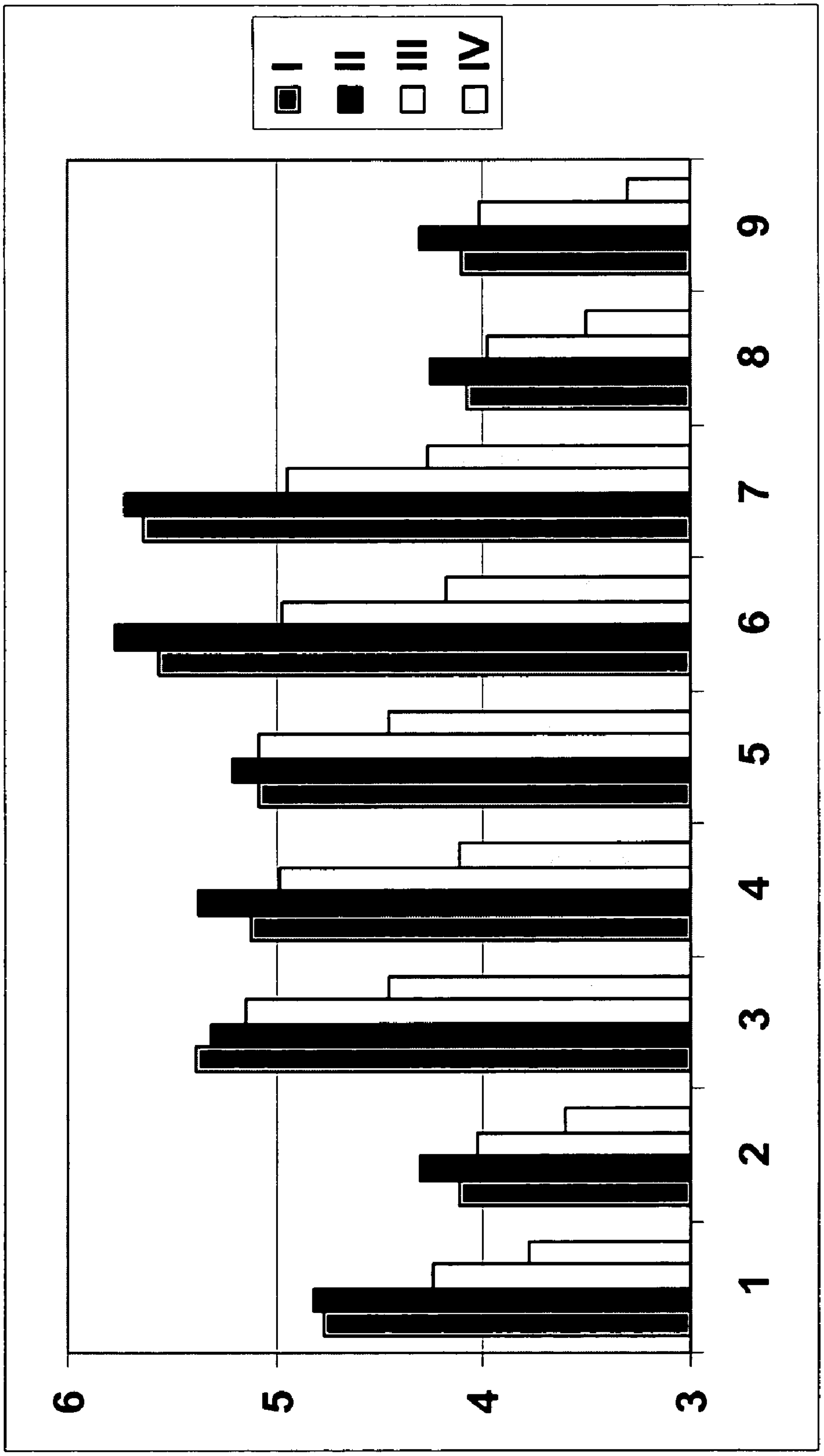
FIG. 4 shows the intensity of musk mixtures from shampoo in use.

FIG. 4 shows the intensity of musk mixtures from shampoo in use. In FIG. 4, numerals I-IV have the following meaning:

I: Intensity from the shampoo

II: Intensity from the shampoo solution

III: Intensity of the wet hair strands

IV: Intensity of the dry hair strands

| | |
|---|---|
| 1 | Pure substance 5 |
| 2 | Pure substance 11 |
| 3 | Mixture of 10:5 in a ratio of 2:1 |
| 4 | Mixture of 12:11 in a ratio of 2:1 |
| 5 | Mixture of 10:11 in a ratio of 1:1 |
| 6 | Mixture of 12:5 in a ratio of 3:2 |
| 7 | Mixture of 12:10 in a ratio of 4:1 |
| 8 | Pure substance 12 |
| 9 | Pure substance 10 |

The mixtures of 10:5 in a ratio of 2:1, 12:11 in a ratio of 2:1, 10:11 in a ratio of 1:1, 12:5 in a ratio of 3:2 and 12:10 in a ratio of 4:1 have the highest intensities from the perfumed shampoo in use.

Perfumes that are exceptional from the hedonistic standpoint and achieve a superior perfume impression are produced with these musk mixtures as fragrances.

Example 3

Assessment of the Perfume of Perfume Mixtures and Single Substances

The assessment of the perfume is carried out from perfume strips. For this purpose perfume strips are dipped into 50% (m/m) solutions of the fragrances or mixtures in isopropyl myristate. The headnote corresponds to the first odor impression and is assessed immediately. The base or also the heartnote develops only after a few minutes (5-10 min.) and accordingly is described later. The assessment of the perfume is carried out by two perfumers.

Individual Substance 10:

The fragrance has a musk type with slight ambrette note, good radiation and unmistakable nitro musk note. The latter provides sweetness, has a positive influence on flowery aspects and provides good adhesion. An animal aspect is pleasantly discernible, without particularly standing out.

Individual Substance 12:

Like individual substance 10, this musk fragrance has a typical nitro musk note (similar to musk ketone, musk xylene) with a slight ambrette note. The term ambrette-like or an ambrette note signifies the similarity to ambrette absolute or musk seed oil. The nitro musk note imparts additional strength, fullness and powderiness to the fragrance.

Individual Substance 5:

This fragrance has a distinct ambrette-like note that is found to be very stirring. This radiation has a particularly positive effect on flowery chords. A not particularly pronounced adhesion and a discrete animal aspect are discernible.

Individual Substance 11:

The odor of 11 is closely related to that of 5, but differs in the somewhat more robust perfume character and better adhesion. The radiation is the same as that of 5, but a waxy subsidiary note is clearly discernible and gives rise to strength, adhesion and sweetness.

Mixture of 10 with 5 in a Ratio of 3:2:

As a result of the addition of 5, this musk chord acquires a more natural character (similarity to musk seed oil), in addition to the pleasant nitro musk note. The radiation is intensified compared with the individual substances. A flowery sweet note is discernible.

Mixture of 10 with 11 in a Ratio of 3:2:

The musk combination radiates a more natural character than 10. The subsidiary note from 11 in combination with the sweetness of the nitro musk note leads to an adhering fullness and strength that cannot be found in this way in the individual substances.

Mixture of 10 with 12 in a Ratio of 3:2:

Both musk fragrances have a typical note of nitro musk that is further intensified by the combination. In this way a strong powdery nature with animal subsidiary note is produced. The fragrances complement one another ideally in perfume oils in which this effect is desired.

Mixture of 12 with 5 in a Ratio of 3:2:

In contrast to the mixture of 10 with 12, this combination shows more strength and natural character in the headnote, without the nitro musk note typical of 12 being lost. The mixture shows strong adhesion and sweetness.

Mixture of 10 with 11 in a Ratio of 3:2:

Similarly to the mixture of 12 with 5, this combination also proves to have a strong and natural headnote. It displays a typical nitro musk note with sweetness and powderiness in the base. Headnote and radiation of the mixture are increased in comparison with the individual substances.

What is claimed is:

1. A mixture comprising two musk fragrances, comprising a mixture of cis/trans-8-cyclohexadecen-1-one (10) and oxacyclohexadecan-2-one (5) present in a ratio having a synergistically enhanced fragrance intensity.

2. A mixture comprising two musk fragrances, wherein said two musk fragrances are selected from the group consisting of:

cis/trans-8-cyclohexadecen-1-one (10) and cis/trans-12/13-oxacyclohexadecen-2-one (11); and cis/trans-8-cyclohexadecen-1-one (10) and oxacyclohexadecan-2-one (5), wherein the ratio of cis/trans-8-cyclohexadecen-1-one to oxacyclohexadecan-2-one or cis/trans-12/13-oxacyclohexadecen-2-one is between about 4:1 and about 1:4.

3. A fragrance composition comprising 0.01-60% by mass of the mixture according to claim 2.

4. A perfumed product comprising a mixture according to claim 2.

5. The perfumed product of claim 4, wherein the product is selected from the group consisting of household products, bodycare products, and perfumery products.

6. The perfumed product of claim 2, wherein said two musk fragrances are cis/trans-8-cyclohexadecen-1-one (10) and cis/trans-12/13-oxacyclohexadecen-2-one (11).

7. The perfumed product of claim 2, wherein said two musk fragrances are cis/trans-8-cyclohexadecen-1-one (10) and oxacyclohexadecan-2-one (5).

8. The perfumed product of claim 3, wherein said two musk fragrances are cis/trans-8-cyclohexadecen-1-one (10) and cis/trans-12/13-oxacyclohexadecen-2-one (11).

9. The perfumed product of claim 3, wherein said two musk fragrances are cis/trans-8-cyclohexadecen-1-one (10) and oxacyclohexadecan-2-one (5).

10. The perfumed product of claim 4, wherein said two musk fragrances are cis/trans-8-cyclohexadecen-1-one (10) and cis/trans-12/13-oxacyclohexadecen-2-one (11).

11. The perfumed product of claim 4, wherein said two musk fragrances are cis/trans-8-cyclohexadecen-1-one (10) and oxacyclohexadecan-2-one (5).

12. The perfumed product of claim 8, wherein the ratio of cis/trans-8-cyclohexadecen-1-one (10) to cis/trans-12/13-oxacyclohexadecen-2-one (11) is between 2:1 and 1:2.

13. The perfumed product of claim 9, wherein the ratio of cis/trans-8-cyclohexadecen-1-one (10) to oxacyclohexadecan-2-one (5) is between 2:1 and 1:2.

14. The perfumed product of claim 10, wherein the ratio of cis/trans-8-cyclohexadecen-1-one (10) to cis/trans-12/13-oxacyclohexadecen-2-one (11) is between 2:1 and 1:2.

15. The perfumed product of claim 11, wherein the ratio of cis/trans-8-cyclohexadecen-1-one (10) to oxacyclohexadecan-2-one (5) is between 2:1 and 1:2.

* * * * *